(12) United States Patent  (10) Patent No.: US 7,205,449 B2
Levin  (45) Date of Patent: Apr. 17, 2007

(54) ADHESIVE BANDAGE INDICATING WOUND CARE INSTRUCTIONS

(75) Inventor: Kenneth Martin Levin, 5 Santa Yorma Ct., Novato, CA (US) 94945

(73) Assignee: Kenneth Martin Levin, Novato, CA (US)

( * ) Notice: Subject to any disclaimer, the term of this patent is extended or adjusted under 35 U.S.C. 154(b) by 864 days.

(21) Appl. No.: 10/005,016

(22) Filed: Dec. 4, 2001

(65) Prior Publication Data

US 2002/0040202 A1 Apr. 4, 2002

(51) Int. Cl.
*A61F 13/00* (2006.01)

(52) U.S. Cl. ............................. 602/58; 602/41; 602/42

(58) Field of Classification Search ............ 602/41–59; 128/888, 889; 604/304–308; 424/443–449
See application file for complete search history.

(56) References Cited

U.S. PATENT DOCUMENTS

| 4,334,530 A | | 6/1982 | Hassell | |
| 4,947,867 A | * | 8/1990 | Keeton | 128/846 |
| 5,181,905 A | * | 1/1993 | Flam | 602/41 |
| 5,261,702 A | * | 11/1993 | Mayfield | 283/115 |
| 5,498,034 A | * | 3/1996 | Ford | 283/67 |
| 5,605,165 A | * | 2/1997 | Sessions et al. | 128/888 |
| 5,897,516 A | * | 4/1999 | Kadash et al. | 602/41 |
| 6,255,553 B1 | | 7/2001 | Sullivan | |
| 2002/0169405 A1 | * | 11/2002 | Roberts | 602/43 |

OTHER PUBLICATIONS

Photocopied Image of Surgical Dressing Manufactured by Corium International, manufactured and sold before filing date of present application. Surgical Dressing includes removable adhesive sticker including the markings "Date_" and "Initials_ ".
Web Page Printout: http://?www.promotionalproducts.net/health_custom_printed_bandages.htm.
Web Page Printout: http://?www.promotionalproducts.net/ bandages.htm.

* cited by examiner

*Primary Examiner*—Kim M. Lewis
(74) *Attorney, Agent, or Firm*—Mark J. Spolyar

(57) ABSTRACT

Adhesive bandage or surgical dressing having markings or indicia providing or associated with wound care instructions. The present invention allows for the placement over a wound an adhesive bandage that clearly indicates information about what treatment the wound or patient should receive.

6 Claims, 1 Drawing Sheet

ADHESIVE BANDAGE INDICATING WOUND CARE INSTRUCTIONS

FIELD OF THE INVENTION

The present invention relates to adhesive bandages or surgical dressings and, more particularly, to bandages or surgical dressings indicating wound care instructions.

BACKGROUND OF THE INVENTION

Cost containment practices in medicine have stretched staffing to a point where fewer nursing professionals are managing more patients. Indeed, tasks that were once performed by licensed professionals are now performed by less qualified staff. In many instances, patients whose mentation is compromised may not be able to participate fully in monitoring the care they receive in the hospital. This problem is exacerbated when patients are transferred to different floors within a facility or between facilities (e.g., from acute to long term care).

For example, assume for didactic purposes, that a patient has suffered brain damage as a result of a cardiac arrest. As part of treatment, a defibrillating pacemaker is implanted in the patient by an acute care facility. The nursing staff at the acute care hospital clearly notes in the patient's chart the necessity to keep the wound dry for five days. When the patient is transferred to a long-term care facility, the nursing staff does not notice the instructions contained in the patient's chart to keep the wound dry for five days, and immediately wants to give him a shower, which would make the wound wet, and create a severe risk of a fatal infection. As the patient was suffering from short-term memory loss, he is not able to remind the nursing staff at the new hospital of the need to keep the wound dry. Assuming there is no other means of warning the nursing staff, the patient is presented with a high risk of serious infection.

The prior art contains adhesive bandages with text markings or other indicia; however, such text markings are generally promotional in nature, such as providing the name and logo of a hospital. In addition, U.S. Pat. No. 6,255,553 teaches an adhesive bandage including a soft three-dimensional figure attached to the outer surface to engage a young child. U.S. Pat. No. 4,334,530 issued to Hassell provides an adhesive strip bandage with markings indicating a recommended direction for removal of the bandage to minimize the chance of reopening a flap wound; however, Hassell does not teach or suggest a bandage that would avoid the problems discussed above. While these bandages fulfill their respective objectives, they do not disclose or suggest a bandage having text markings or other indicia providing care instructions for a wound.

In light of the foregoing, a need in the art exists for adhesive bandages and surgical dressings that indicate care instructions to help avert the type of problems discussed above. The present invention substantially fulfills this need.

SUMMARY OF THE INVENTION

The present invention is an adhesive bandage or surgical dressing having markings or indicia providing or associated with wound care instructions. As the description below provides, the present invention allows for the placement over a wound an adhesive bandage that clearly indicates information about what treatment the wound or patient should receive.

DESCRIPTION OF PREFERRED EMBODIMENT(S)

Figure 1:
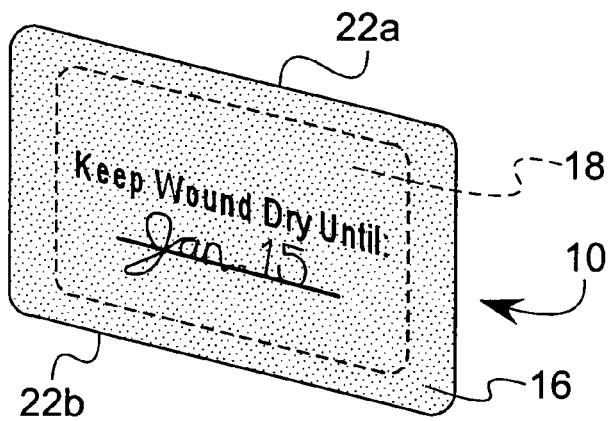
FIG. 1 is a perspective view of an adhesive bandage according to an embodiment of the present invention.

FIGS. 1 thru 4 illustrate adhesive bandages according to various embodiments of the present invention. As FIG. 1 illustrates, the present invention is directed to an adhesive bandage or surgical/wound dressing 10 comprising an adhesive-coated backing 16 on which an absorbent pad 18 intended to be placed over a wound is medially disposed between transverse edges 22a, 22b of backing 16. In one embodiment, backing 16 comprises a flexible backing coated on one side with a pressure-sensitive adhesive. Absorbent pad 18 is typically made of sterile gauze or the like and is carried on the adhesive-faced side, usually medially positioned between the transverse edges 22a, 22b as shown. As is conventional, a pair of removable release sheets are generally provided to protect the adhesive face and the absorbent pad during storage and prior to application to a wound of a patient. As the Figures provide, the bandage of the present invention is provided with markings, on the non-adhesive side of backing 16, indicating wound care instructions.

As FIG. 1 illustrates, the markings may be text markings providing wound care instructions printed directly on the non-adhesive side of backing 16. For example, the text markings may provide proscriptive care instructions, such as "Keep Wound Dry" readily indicating to nursing staff that the underlying wound should be kept dry. In another embodiment, the text markings may provide "Keep Wound Dry Until _____", where a date could be written on the line marking. Other examples of text markings include: "Change Bandage Every 24 hours;" "Measure Infected Area Every 24 Hours and Notify Physician if Infected Area Grows;" "Change Bandage on _____;" and "Keep Bandaged until _____." Of course, any suitable text-based wound care instruction can be printed on the bandage of the present invention. The indicia or markings may be applied to the bandage in various ways. For example, they can be applied by carving, engraving or etching into the surface of backing 16, or preferably by means of suitable inks, dyes, or pigments which should optimally be relatively fast, water-insoluble and non-toxic. Such inks or dyes may be applied, for example, by gravure or any other known printing technique.

Figure 2:
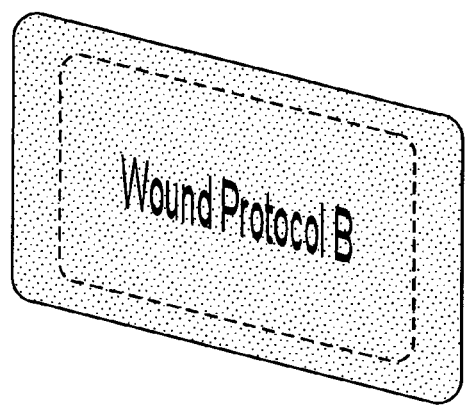
FIG. 2 is a perspective view of an adhesive bandage having care instructions that reference a wound protocol.

As FIG. 2 provides, the text messages may also reference wound care protocols. Typically, such wound care protocols would be specific to a particular medical field, hospital department, or industry. A typical message might read: "Wound Protocol B Until _____." To implement the system enabled by the bandage of the present invention, a hospital or other care facility maintains a supply of bandages according to the invention. In one form, each bandage in the supply includes a reference to one of several wound protocols. The hospital associates such wound protocol references (e.g., Wound Protocol B) to at least one care instruction, such as "Keep Wound Dry," or "Change Bandage Every 24 Hours." The hospital then instructs its staff, either directly or by providing procedure manuals, training materials, and the like, as to what set of care instructions are associated with each wound protocol reference. In treating a patient, hospital staff then applies the bandage to the wound of the patient marked with the desired or appropriate wound protocol.

By making the printed message reference a protocol, one marking could serve different purposes in different facilities allowing for manufacturing economies of scale while preserving flexibility in the application. For example, one hospital could associate "Wound Protocol B" with a set of care instructions including: 1) Keep Wound Dry for at least 5 Days; and 2) Change Bandage Daily. Another care facility may associate an entirely different set of care instructions to the same protocol designation.

Figure 3:
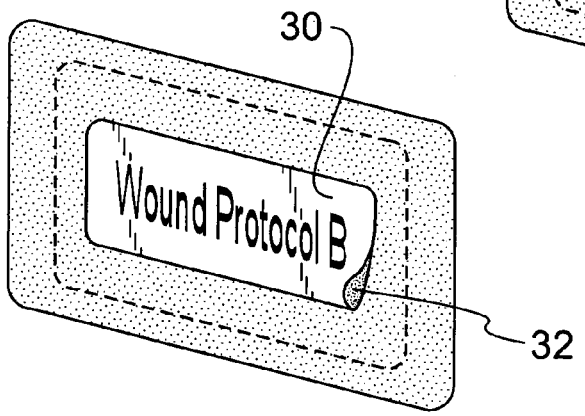
FIG. 3 is a perspective view of an adhesive bandage according to another embodiment of the present invention.

FIG. 3 provides an alternative embodiment of the present invention, allowing for the same labeling benefits at, potentially, a reduced cost. Specifically, an adhesive label 30 can be applied to the non-adhesive side of backing 16 of a standard adhesive bandage. As FIG. 3 provides, adhesive label 30 includes markings indicating care instructions for a wound. In one embodiment, adhesive label 30 is pre-printed with markings indicating care instructions. In one form, adhesive label 30 can be one of several labels formed on a release sheet. Backing 32 of adhesive label 30 can be made out of the same bandage material as backing 16 or any other suitable material. Accordingly, hospital staff may apply a standard bandage or dressing and affix thereto pre-printed adhesive label 30. For example, a bandage applied to an incision may be affixed with an adhesive label indicating: "Keep Wound Dry Until _____." In one embodiment, adhesive label 30 is dimensioned to fit within the surface area provided by backing 16. For instance, bandage 10 may be 3 inches wide by 4 inches long, while adhesive label may be 1 inch wide and 2 inches long.

Figure 4:
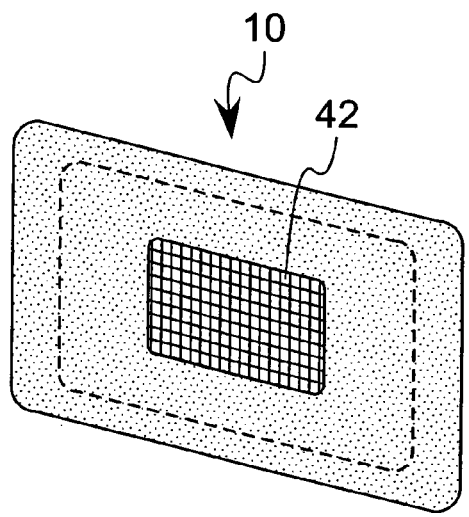
FIG. 4 is a perspective view of an adhesive bandage having a color marking associated with a care instruction or protocol.

FIG. 4 illustrates another embodiment of the present invention where bandage 10 includes color markings indicating care instructions. As FIG. 4 shows, bandage 10 includes color marking 42 associated with a wound care protocol or other wound care instruction. For example and in one embodiment, the color marking 42 on bandages 10 may include one of a variety of colors, where each color is associated with a particular wound care protocol (see above).

In another embodiment, each color may be associated with a date or time value. In one form, a hospital maintaining a supply of bandages according to the present invention, wherein each bandage in the supply is marked with one of seven different colors and the supply includes bandages from all of the seven different colors. According to written protocols or instructions, the hospital associates each of the seven different colors with a different day of the week. Accordingly, the current day of the week determines which color bandages are applied. For example, the bandage may be marked with the color associated with the current day of the week. Alternatively, the bandage may be marked with the color associated with the day of the week on which removal of the bandage is intended.

For example, it is common practice to change IV dressings every 3 days. One way to make sure the bandage is changed is to mark the bandage with a text legend and a date that the bandage was applied or the date that it should be changed. Hospital protocol will determine how the bandage should be marked. An alternate to marking a bandage with a date is to color code the seven days of the week. A bandage with a yellow color code may represent Monday, and green color code may represent Tuesday, and so on. The bandage according to this embodiment will readily alert a health care staff member that something may be wrong if a patient has a green coded IV bandage on Friday (4 days after Tuesday) and may then take appropriate steps to change the IV dressing. Alternatively, the color could represent the day the bandage should be changed so a three-day bandage applied on Tuesday would have Thursday's color. Accordingly, hospital staff need only look at the color of the bandage to determine whether it should be changed. In one such embodiment, the text markings provide a line allowing nursing staff to add the date on which the bandage was applied to minimize any confusion (e.g., so a nurse on a Friday, for example, will not confuse a bandage including markings representing Thursday as a bandage that should be kept on until the following Thursday.

A variety of other configurations are possible. Such color markings can be used in addition to or instead of text markings and can be adapted to a flexible array of uses according to written hospital protocols. In addition, the backing layer of the bandage can be printed with inks or other chemicals that change color as they are exposed to air and oxidize, or to ultraviolet rays (such as thermo-chromatic inks). When the bandage has changed its shading to a specific color or shade of color it acts as a signal to the care provider that it should be changed. In another embodiment, a small LCD timer is affixed to the non-adhesive side of backing 16. The timer, in one embodiment, counts up by the hour/minute from the point in time the bandage was applied. In another embodiment, the timer counts down to a time the bandage should be changed.

Lastly, although the Figures show a particular form of bandage, the present invention can be implemented on any suitable bandage such as an adhesive strip bandage or surgical dressing of any shape or size. Accordingly, the present invention has been described with reference to specific embodiments. Other embodiments of the present invention will be apparent to one of ordinary skill in the art. It is, therefore, intended that the claims set forth below not be limited to the embodiments described above.

What is claimed is:

1. A method allowing for a visible indication that a bandage should be changed, the method comprising the steps of:
   maintaining a supply of bandages, wherein each bandage in said supply is marked with one of seven different colors, and wherein said supply of bandages indudes bandages from all of the seven different colors;
   associating each of the seven different colors with a different day of the week; and
   applying one of said bandages to a patient, wherein the bandage is marked with the color associated with the then-current day of the week.

2. A method allowing for a visible indication that a bandage should be changed, the method comprising the steps of:
   maintaining a supply of bandages, wherein each bandage in said supply is marked with one of seven different colors, and wherein said supply of bandages includes bandages from all of the seven different colors;
   associating each of the seven different colors with a different day of the week; and
   applying one of said bandages to a patient, wherein the bandage is marked with the color associated with the day of the week on which removal of said bandage is intended.

3. A method allowing for a visible indication that a bandage should be changed, the method comprising the steps of:

maintaining a supply of bandages, wherein each bandage in said supply is marked with one of set of different markings, and wherein said supply of bandages includes bandages from all of the set of different markings;

associating each marking of the set of different markings with a different wound protocol; and applying one of said bandages to a wound of a patient, wherein the bandage is marked with the marking associated with a desired wound protocol to be applied to the wound.

4. The method of claim 3 wherein the markings are text markings.

5. The method of claim 3 wherein the markings are color markings.

6. The method of claim 3 wherein the markings are symbols.

* * * * *